(12) United States Patent
Ning et al.

(10) Patent No.: US 8,229,246 B2
(45) Date of Patent: *Jul. 24, 2012

(54) METHOD AND APPARATUS FOR 3D METAL AND HIGH-DENSITY ARTIFACT CORRECTION FOR CONE-BEAM AND FAN-BEAM CT IMAGING

(75) Inventors: Ruola Ning, Fairport, NY (US); Yan Zhang, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,289

(22) Filed: Sep. 19, 2011

(65) Prior Publication Data

US 2012/0008845 A1    Jan. 12, 2012

Related U.S. Application Data

(63) Continuation of application No. 12/045,552, filed on Mar. 10, 2008, now Pat. No. 8,023,767.

(51) Int. Cl.
*G06K 9/00* (2006.01)
(52) U.S. Cl. ......... 382/275; 382/128; 382/131; 382/154
(58) Field of Classification Search .................. 382/128, 382/131, 275
See application file for complete search history.

(56) References Cited

U.S. PATENT DOCUMENTS

| | | | |
|---|---|---|---|
| 3,165,630 A | 1/1965 | Bielat et al. | |
| 3,973,126 A | 8/1976 | Redington et al. | |
| 4,015,836 A | 4/1977 | Redington et al. | |
| 5,170,439 A | 12/1992 | Zeng et al. | |
| 5,375,156 A | 12/1994 | Kuo-Petravic et al. | |
| 5,448,607 A | 9/1995 | McKenna | |
| 5,459,769 A | 10/1995 | Brown | |
| 5,526,394 A | 6/1996 | Siczek et al. | |
| 5,564,438 A | 10/1996 | Merchant | |
| 5,602,891 A | 2/1997 | Pearlman | |
| 5,609,152 A | 3/1997 | Pellegrino et al. | |
| 5,784,481 A | 7/1998 | Hu | |
| 5,802,137 A | 9/1998 | Wilkins et al. | |
| 5,909,476 A * | 6/1999 | Cheng et al. | 378/4 |

(Continued)

FOREIGN PATENT DOCUMENTS

CN    101622526 A    1/2010

(Continued)

OTHER PUBLICATIONS

Weitkamp et al., "X-ray phase imaging with a grating interferometer", Optics Express, 2005, pp. 6296-6304, vol. 13, Issue 16.

(Continued)

*Primary Examiner* — Tom Y Lu
(74) *Attorney, Agent, or Firm* — Blank Rome LLP

(57) ABSTRACT

A 3D metal artifacts correction technique corrects the streaking artifacts generated by titanium implants or other similar objects. A cone-beam computed tomography system is utilized to provide 3D images. A priori information (such as the shape information and the CT value) of high density sub-objects is acquired and used for later artifacts correction. An optimization process with iterations is applied to minimize the error and result in accurate reconstruction images of the object.

19 Claims, 5 Drawing Sheets

302    304    306

U.S. PATENT DOCUMENTS

| | | | |
|---|---|---|---|
| 5,999,587 | A | 12/1999 | Ning et al. |
| 6,002,738 | A | 12/1999 | Cabral et al. |
| 6,014,419 | A | 1/2000 | Hu |
| 6,018,564 | A | 1/2000 | Wilkins et al. |
| 6,047,042 | A | 4/2000 | Khutoryansky et al. |
| 6,049,343 | A | 4/2000 | Abe et al. |
| 6,075,836 | A | 6/2000 | Ning |
| 6,125,193 | A * | 9/2000 | Han ............................... 382/131 |
| 6,282,256 | B1 | 8/2001 | Grass et al. |
| 6,298,110 | B1 | 10/2001 | Ning |
| 6,298,114 | B1 | 10/2001 | Yoda |
| 6,477,221 | B1 | 11/2002 | Ning |
| 6,480,565 | B1 | 11/2002 | Ning |
| 6,504,892 | B1 | 1/2003 | Ning |
| 6,618,466 | B1 | 9/2003 | Ning |
| 6,987,831 | B2 | 1/2006 | Ning |
| 7,023,951 | B2 * | 4/2006 | Man ................................. 378/8 |
| 7,103,135 | B2 * | 9/2006 | Koppe et al. ...................... 378/4 |
| 7,245,755 | B1 | 7/2007 | Pan et al. |
| 7,636,461 | B2 * | 12/2009 | Spies et al. .................... 382/128 |
| 7,697,660 | B2 | 4/2010 | Ning |
| 2003/0073893 | A1 | 4/2003 | Hsieh |
| 2004/0081273 | A1 | 4/2004 | Ning |
| 2005/0286680 | A1 | 12/2005 | Momose |
| 2006/0039532 | A1 | 2/2006 | Wu et al. |
| 2006/0094950 | A1 | 5/2006 | Ning |
| 2007/0053477 | A1 | 3/2007 | Ning |
| 2007/0183559 | A1 | 8/2007 | Hempel |
| 2007/0253528 | A1 | 11/2007 | Ning et al. |

FOREIGN PATENT DOCUMENTS

| | | |
|---|---|---|
| EP | 0 948 930 A1 | 10/1999 |
| EP | 1 149 559 A1 | 10/2001 |
| WO | 93/17620 A1 | 9/1993 |
| WO | 99/01066 A1 | 1/1999 |
| WO | 0135829 A1 | 5/2001 |
| WO | 2007100823 A2 | 9/2007 |

OTHER PUBLICATIONS

Faris et al., "Three-dimensional beam-deflection optical tomography of a supersonic jet", Applied Optics, 1988, pp. 5202-5212, vol. 27, Issue 24.

Wu et al., "X-Ray Cone-Beam Phase Tomography Formulas Based on Phase-Attenuation Duality", Optics Express, Aug. 2005, pp. 6000-6014, vol. 13, No. 16.

Momose, A., "Demonstration of Phase-Contrast X-Ray Computed Tomography Using an X-Ray Interferometer", Nuclear Instruments and Methods in Physics Research Section A, Mar. 1994, pp. 622-628, vol. 352, Issue 3.

Mayo et al., "X-Ray Phase-Contrast Microscopy and Microtomography", Optics Express Sep. 2003, pp. 2289-2302, vol. 11, No. 19.

Chapman et al., "Diffraction Enhanced X-Ray Imaging", Physics in Medicine and Biology, Aug. 1997, pp. 2015-2025, vol. 42, No. 11.

Jaffray et al., "Performance of a Volumetric CT Scanner Based Upon a Flat-Panel Imager", Proceedings of the 1999 Medical Imaging Physics of Medical Imaging Conference, May 28, 1999, pp. 204-214, vol. 3659, No. I, chapter 2 "CBCT System", San Diego, CA, USA.

European Search Report and Opinion issued in EP 10185587, dated Nov. 29, 2010 (6 pages).

First Chinese Office Action and translation issued in Chinese Patent Application No. 200780013865.X, dated Oct. 29, 2010 (7 pgs).

First European Office Aciton issued in European Patent Application No. 00978341.6, dated Sep. 4, 2007 (2 pgs).

Examination Report issued in EP 02 720 960.0-1224, dated Jul. 14, 2008 (2 pages).

First Office Action for European Patent Application No. 02 720 96.0, dated Dec. 29, 2006 (4 pages).

First, Second, Third and Fourth Chinese Office Actions issued in Chinese Patent Application No. 200380103101.1 and dated Nov. 23, 2007 (25 pages), Aug. 1, 2008 (7 pages), Jun. 12, 2009 (7 pages), and Jan. 10, 2010 (4 pages) respectively.

Nath, et al., "Wavelet based compression and denoising of optical tomography", Aug. 15, 1999, pp. 37-46, vol. 167, Issues 1-6.

Supplementary Partial European Search Report for EP 03 78 3247, dated Dec. 7, 2009 (6 pages).

Boone et al.,"Dedicated Breast CT: Radiation Dose and Image Quality Evaluation", Radiology, Dec. 2001, pp. 657-667, vol. 221, No. 3.

Examination Report issued in EP 03 783 247.4-1265, dated Feb. 26, 2010 (3 pages).

First Office Action issued in Chinese Patent Application No. 200810171361.7, dated Apr. 14, 2010 (9 pages).

European Search Report for EP 10013992.2-1265, dated Dec. 22, 2010 (7 pages).

Chen et al., "Cone-beam volume CT breast imaging: Feasibility Study", Medical Physics, May 2002, pp. 755-770, vol. 29, Issue 5, AIP, Melville, NY, US.

Extended Search Report for EP 10013992.2-1265, dated Dec. 15, 2010 (7 pages).

Anderson et al., "An Interactive Computer Graphics System for the Computed Tomographic Breast Scanner (CT/M)", 1979, pp. 350-354.

Chang et al., "Computed Tomography of the Breast", Radiology, 1977, pp. 827-829, vol. 124, No. 3.

Chang et al., "Computed Tomographic Evaluation of the Breast", American Journal of Roentgenology, pp. 459-484, vol. 131.

Chang et al., "Computed Tomography in Detection and Diagnosis of Breast Cancer," Cancer, August Supplement, 1980, pp. 939-946, vol. 46.

Feldkamp et al, "Practical Cone-Beam Algorithm," Journal of the Optical Society of America, Jun. 1984, pp. 612-619, vol. 1, No. 6.

Hu, "A New Cone Beam Reconstruction Algorithm for the Circular Orbit," IEEE Nuclear Science Symposium and Medical Imaging Conference 1994 conference Record, 1995, pp. 1261-1265, vol. 3.

Hu, "Exact Regional Reconstruction of Longitudinally-Unbounded Objects using the Circle-and Line Cone Beam Tomographic System," SPIE, 1997, pp. 441-444, vol. 3032.

Kak et al., "Principles of Computerized Tomographic Imaging", Classics in Applied Mathematics, 1988, pp. 99-107, Siam.

Kornmesser et al., "Fast Feldkamp-reconstruction for Real-time Reconstruction Using C-arm Systems, " Proceedings of the 16th International Congress and Exposition on Computer Assisted Radiology and Surgery (CARS 2002), 2002, pp. 430-434 ISBN 3-540-43655-3.

Tang et al., "A Three-dimensional Weighted Cone Beam Filtered Back Projection (CB-FBP) Algorithm for Image Reconstruction in a Volumetric CT Under a Circular Source Trajectory", Physics in Medicine and Biology, Aug. 3, 2005, pp. 3889-3906, vol. 50.

Yang, et al., "Modified FDK half-scan (MFDKHS) Scheme on Flat Panel Detector-Based Cone-Beam CT," Apr. 2005, SPIE vol. 5745, Proceedings of Medical Imaging 2005: Physics in Imaging held Feb. 13, 2005, pp. 1030-1037.

Yang, et al., "Implementation & Evaluation of the Half-Scan Scheme Based on CBCT (Cone-Beam CT) System", 2004, SPIE vol. 5368, Proceedings of Medical Imaging 2004: Physics, pp. 542-551.

Yu et al., "Application of Asymmetric Cone-beam CT in Radiotherapy", 2004, IEEE Nuclear Science Symposium Conference Record 2004, pp. 3249-3252, vol. 5.

Zhao et al., "Feldkamp-Type Cone-Beam Tomography in the Wavelet Framework", IEEE Transactions on Medical Imaging, Sep. 2000, pp. 922-929, vol. 19, Issue 9.

* cited by examiner 302　　304　　306

METHOD AND APPARATUS FOR 3D METAL AND HIGH-DENSITY ARTIFACT CORRECTION FOR CONE-BEAM AND FAN-BEAM CT IMAGING

REFERENCE TO RELATED APPLICATION

The present application is a continuation of U.S. patent application Ser. No. 12/045,552, filed Mar. 10, 2008, currently pending, whose disclosure is hereby incorporated by reference in its entirety into the present disclosure.

STATEMENT OF GOVERNMENT INTEREST

The work leading to the present invention was funded by the NIH under Agreement Nos. R01 9 HL078181 and P50 AR054041. The government has certain rights in the invention.

FIELD OF THE INVENTION

The present invention is directed to CT imaging and more particularly to the correction of high-density artifacts in such imaging.

DESCRIPTION OF RELATED ART

Bone grafting is a common procedure in orthopedic surgery. As shown in FIG. 1, a bone graft 102 is grafted between bone hosts (portions of the patient's original bone) 104 and 106. The bone graft 102 is held in place by a titanium plate 108 and titanium screws 110 until the bone graft 102 and the bone hosts 104, 106 grow together.

Orthopaedists have developed a method to prevent the future failure of reconstruction surgery by revitalizing structural grafts to improve their biomechanical properties. Through using certain combinations of viruses and drugs they can introduce angiogenic, osteogenic and remodeling signals onto the cortical surface of the grafts. Therefore, the volume growth of contiguous new bone that spans the host-graft-host junction is the most important parameter to accurately assess bone healing.

With the capability for 3D imaging of large volumes with isotropic resolution, the CBCT (cone-beam computed tomography) imaging technique is helpful to determine that parameter. However, the titanium plates and screws used to connect structural grafts with host bones (as seen in FIG. 1) cause streaking and shading artifacts in the reconstructed images due to their high attenuation of x-rays. These artifacts will distort the information of bones and cause difficulties and errors when measuring their growth. The main reason for these artifacts is the beam hardening caused by metal implants' high attenuation of x-rays.

High orders of metal projections are usually used to compensate for the effect of beam hardening. In order to get the metal-only projection, grey-level thresholding is commonly used on the reconstructed images to segment metals out, which will be forward-projected onto the detector. However, due to the large size of the titanium plate and screws used by orthopaedists in the reconstruction surgery, streaking artifacts are usually so severe that thresholding cannot carry out the metal segmentation without including artifacts in the segmented image.

SUMMARY OF THE INVENTION

To solve this problem and help orthopaedists correctly monitor the growth of host-graft-host junctions, the present invention is directed to a 3D metal artifacts correction technique to correct the streaking artifacts generated by titanium implants or other similar objects. This 3D technique can be generalized for any correction of the artifacts caused by high density sub-objects, such as metal implants in orthopedic surgery and isotope seeds in cancer treatments (for example, prostate and/or breast cancer treatments).

The novelty of this technique lies in three parts. Firstly, a CBCT system is utilized to provide 3D images; hence this 3D technique can deal with high density artifacts globally. Secondly, a priori information (such as the shape information and the CT value) of high density sub-objects is acquired and used for later artifacts correction. Finally, an optimization process with iterations is applied to minimize the error and result in accurate reconstruction images of the object.

The present invention can be implemented along with the technologies disclosed in U.S. Pat. Nos. 5,999,587, 6,075,836, 6,298,110, 6,477,221, 6,480,565, 6,504,892, 6,618,466, and 6,987,831 and U.S. Patent Application Publications 2007/0053477 and 2007/0253528, all of which are hereby incorporated by reference in their entireties into the present disclosure.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
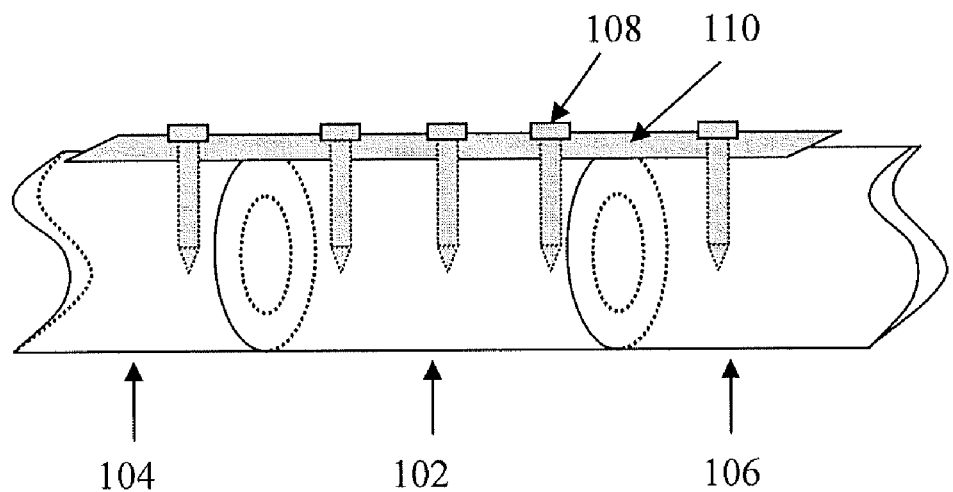
FIG. 1 shows the use of a titanium plate and screws to secure a bone graft between bone hosts.

A preferred embodiment of the present invention will be set forth in detail with reference to the drawings, in which like reference numerals refer to like elements or steps throughout.

Figure 2:
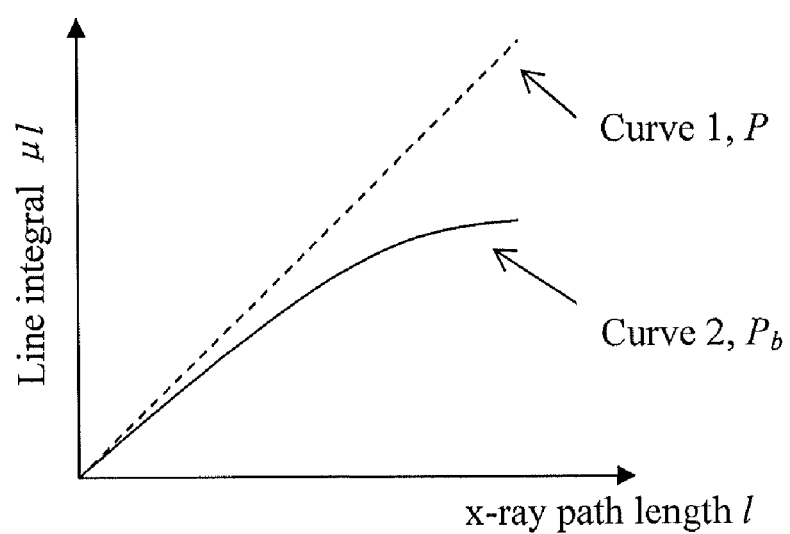
FIG. 2 shows line integrals with and without beam hardening.

Metal artifacts are mainly due to the beam hardening caused by high attenuation of x-rays of metal implants. Because more low-energy photons are absorbed by metal, the x-ray beam becomes more penetrating and thus the attenuation coefficient of the object along the x-ray path appears smaller and smaller along the x-ray path. Therefore, the line integral is not linear to the length of the x-ray path anymore. Instead, it gets smaller as the x-ray path gets longer, as illustrated in FIG. 2.

Figures 3A, 3B:
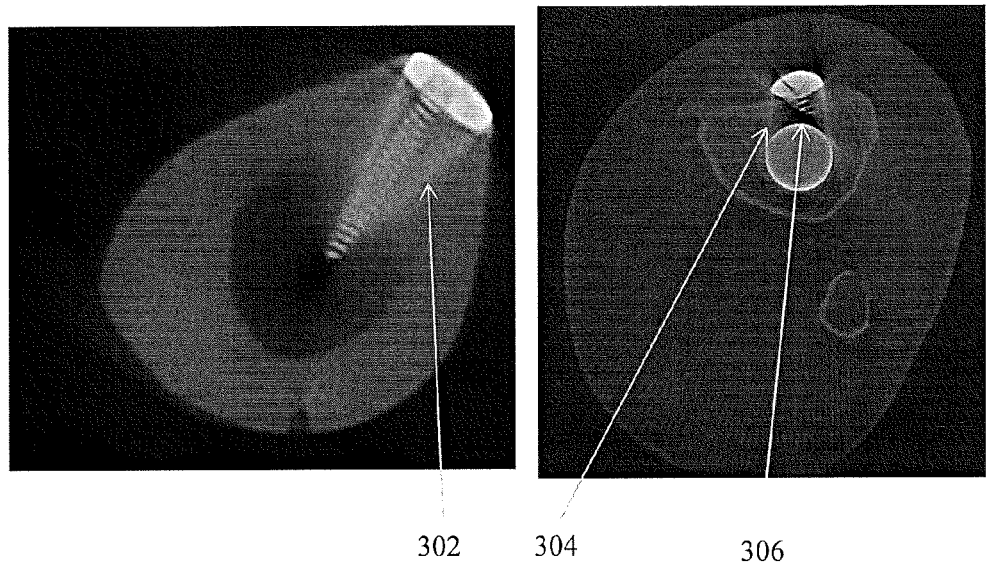
FIGS. 3A and 3B show reconstructed images with streaking and shading artifacts.

Since there are discrepancies between the projection rays that pass through only one of the dense objects and the rays that pass through multiple objects, dark banding artifacts and streaking artifacts appear, as seen in FIGS. 3A and 3B, which show streaking artifacts 302 and 304 and shading artifacts 306. In order to correct these artifacts, the line integral of the metal with beam hardening (as seen in curve 2, $P_b$, in FIG. 2) needs to be corrected back to a linear relationship with the x-ray path length (as seen in curve 1, P, in FIG. 2).

Theoretically, any smooth, monotonically increasing concave function like $P_b$, can be mapped onto a straight line by the following operation:

$$P = P_b + \sum_{i=2}^{+\infty} \alpha_i P_b^i, \qquad (1)$$

where $\alpha_i$ is the coefficient of the $i^{th}$ polynomial term. These coefficients are dependent on the material and the spectrum of the x-ray tube. They can be determined by the experiment described as follows. The material of simple shape, for example, sphere or cylinder, is scanned and reconstructed to provide its images for the calculation of the x-ray path length at each detector cell. The material's projection image is then acquired with given x-ray spectrum and high mAs to calculate the line integral image containing beam hardening. The line integral value is plotted as function of the x-ray path length for all detector pixels. This curve corresponds to curve 2, $P_b$, in FIG. 2. In order to get curve 1, P, in FIG. 2, the linear attenuation coefficient of the material at the average energy of the given x-ray spectrum, μ, is obtained from the NIST (National Institute of Standards and Technology) X-ray Attenuation Database. And then, curve 1, P, in FIG. 2, can be plotted as P=μ·l, where l is the x-ray path length at each detector pixel. Once $P_b$ and P are obtained, $\alpha_i$ can be determined by minimum least-squares fit, using the nonlinear curve $P_b$ as the independent variable and the straight line P as the dependent variable. Usually the second and the third order polynomial terms of $P_b$ are enough to correct most artifacts.

As discussed just above, the line integral of the metal (high density object) containing beam hardening, denoted by $P_m$, needs to be acquired first to correct the beam hardening caused by the metal. This can be achieved by segmenting the metal (high density object) from the reconstructed images and forward-projecting it onto the detector. The forward-projected metal projection is the line integral of the metal containing beam hardening. Once $P_m$ is obtained, using Eq. (1) can get the corrected projection data:

$$P_{corrected} = P_{original} + \alpha_1 P_m^2 + \alpha_2 P_m^3, \qquad (2)$$

where $P_{original}$ represents the original projection of the whole scanned object, including metal, bone and soft tissue, etc. $P_{corrected}$ represents the projection with the correction of beam hardening caused by the metal.

Figure 4B:
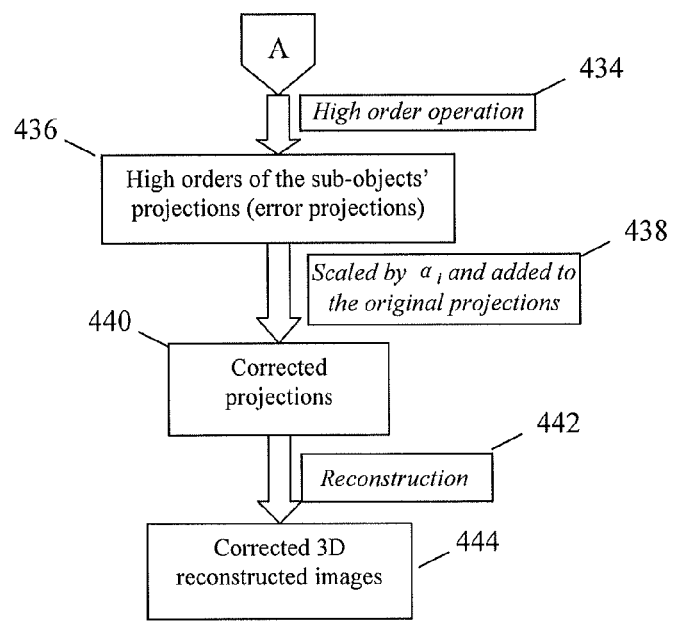
FIGS. 4A and 4B show a flow chart of the metal beam-hardening correction process.
Figure 4A:
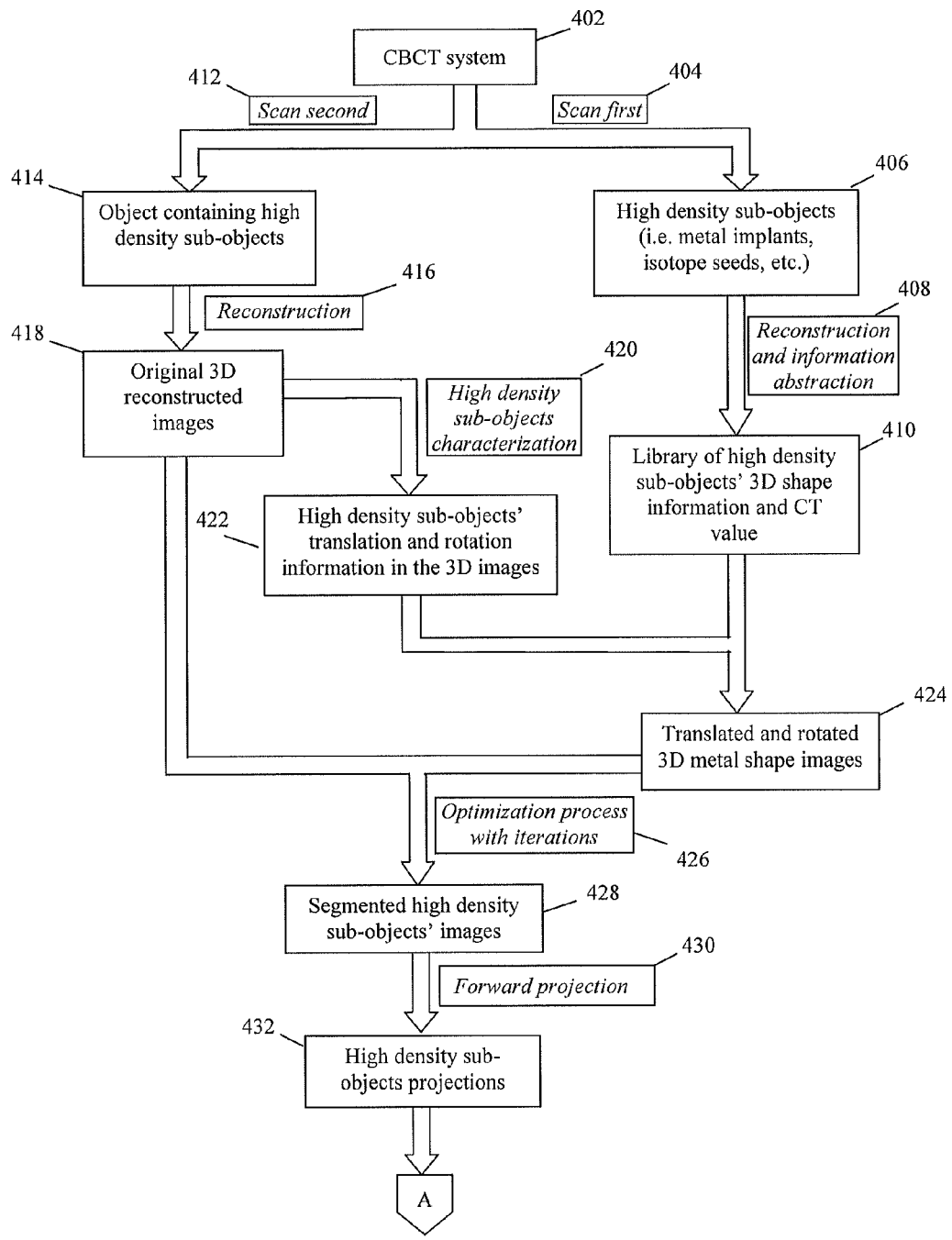

After the corrected projections are obtained, they will be back-projected to reconstruct the artifacts-corrected images. The correction process can be summarized as follows, with reference to the flow charts of FIGS. 4A and 4B.

A CBCT system is provided in step 402. A first scan in step 404 yields high-density sub-objects (e.g., metal implants, isotope seeds, or the like) in step 406. Reconstruction and information abstraction in step 408 yield a library of high-density sub-objects' 3D shape information and CT value in step 410.

A second scan in step 412 yields image data for an object containing high-density sub-objects in step 414. Reconstruction in step 416 yields original 3D reconstructed images in step 418. High-density sub-object characterization in step 420 yields translation and rotation information concerning the high-density sub-objects in the 3D images in step 422.

The translation and rotation information from step 422 and the library from step 410 are used to form translated and rotated 3D metal shape images in step 424. An optimization process with iterations in step 426 yields segmented high-density sub-object images in step 428. Forward projection in step 430 yields high-density sub-object projections in step 432. A high-order operation in step 434 yields high orders of the sub-objects' projections (error projections) in step 436. The error projections are scaled by $\alpha_i$ and added to the original projections in step 438 to yield corrected projections in step 440. The corrected projections are used in a reconstruction in step 442 to yield corrected 3D reconstructed images in step 444.

The novelty of this invention lies in three parts.

Firstly, a CBCT system is utilized to provide 3D images; hence this 3D technique works on 3D images and deals with high density artifacts globally. Conventional methods usually work on 2D images and correct the high density artifacts slice by slice.

Secondly, a priori information (such as the shape information and the CT value) of high density sub-objects is acquired and used for later artifacts correction. During the correction of beam hardening caused by high density sub-objects, the segmentation of those sub-objects from the reconstructed images is important. Usually, when beam hardening is not very severe, using grey-level thresholding can easily do the work since those sub-objects have very high CT values. But when a high density sub-object is large, beam hardening will be severe that its CT value drops and streaking artifacts are serious. Hence, using thresholding can not segment the whole sub-object out, and some severe artifacts may be included.

To solve this problem, our 3D metal artifacts correction technique uses a 3D library which contains those high density sub-objects' shape information to help to do the segmentation. This library can be set up before high density sub-objects are implanted. During the acquisition of this a priori information, a high x-ray technique can be chosen to reduce beam hardening as much as possible, i.e. highest kVp with beam filters and highest mAs. The reconstructed images will be processed, and the 3D shape information of the sub-object will be stored as binary images in the library. When an object containing high density sub-objects is scanned, 3D shape information of the sub-objects will be retrieved from the library and registered with the object's images to help to do the segmentation. Since the high density sub-objects will be placed in the scanned object in various positions, the 3D library needs to be rotated and translated to register with the reconstructed images. In order to do so, the characteristics of the sub-objects, such as the long axis and the short axis of the metal plate and the axes of the nails, will be identified in the object's images to provide the rotation and the translation information of high density sub-objects. This information will be used to register the 3D library with the object's reconstructed images to do the segmentation.

Thirdly, an optimization process with multiple iterations is applied to minimize the segmentation error, and accurate reconstruction images of the object can finally result from the 3D correction technique. To segment the high-density objects from the reconstructed images, it is important to accurately register the shape information of the high-density sub-objects in the library with the reconstructed images. Therefore, an optimization process with iterations is applied here to minimize the segmentation error. Firstly, high density objects are roughly segmented from reconstruction images by thresholding method to approximate their translation and rotation information. Although thresholding might include some artifacts, the orientation information of the high density objects can be obtained from this initial segmentation to guide the registration. The shape images in the library are then translated and rotated basing on the initially obtained orientation information to register with the high-density objects. Three-dimensional convolution is performed between the rotated shape images and the initially segmented high-density objects to calculate the registration error. An iteration process is used to rotate and translate the shape images within a small range and the registration error is calculated at each time. The iteration process stops once the smallest registration error is achieved and the orientation information at that moment is recorded. The shape images in the library are finally translated and rotated basing on the optimized orientation information to segment the high density objects from the reconstructed images.

It is worth pointing out here that the metal library only contains binary images and the sub-objects' CT values; thus, it does not consume much storage resource and can be easily updated by just adding new information into it. In addition, an individual library can be set up to provide particular high-density sub-objects' information for each patient case to do continuous studies or treatments.

Figure 5A:
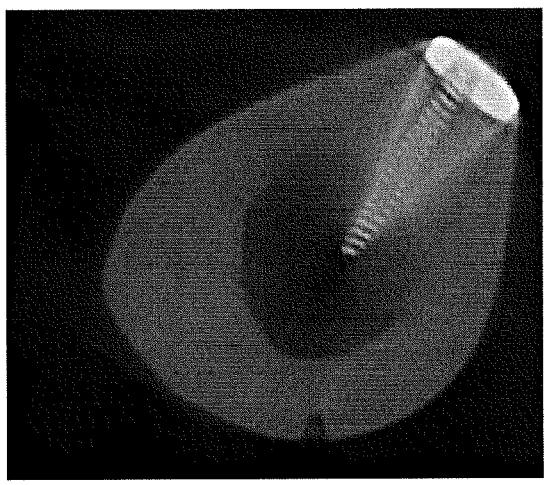
FIGS. 5A and 5B show images without correction.
Figure 5B:
Figure 5C:
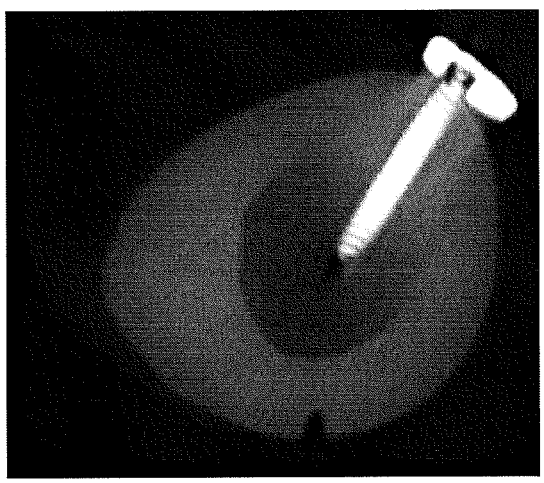
FIGS. 5C and 5D show corresponding images with correction.
Figure 5D:

FIGS. 5A-5D compare original images with the corrected images. The images in the top row (FIGS. 5A and 5B) are the original images, while the images in the bottom row (FIGS. 5C and 5D) are the corrected images. As can be seen, metal objects such as pins are much more clearly visible, and artifacts are greatly reduced. The metals (i.e. the titanium rod, the titanium plate and the pins) are firstly scanned by cone-beam system with highest x-ray technique (i.e. highest kVp, highest mAs and beam filter) to minimize beam hardening as much as possible. Their three-dimensional reconstructed images are stored as binary shape images (in which "1" represents the high-density sub-object and "0" represents air) in an image library in storage. When the object (as seen a bone phantom in FIG. 5A and a patient leg in FIG. 5B) containing those high density sub-objects is scanned by the cone-beam system, the images containing beam hardening artifacts are reconstructed and shown in FIG. 5A-B. Then high density sub-objects' orientation in the object (i.e. the axes of the titanium plate, the nails and the rod) is acquired from the 3D reconstructed images. The image library which was set up previously is recalled from the storage to provide the shape images of high density sub-objects. The shape images are rotated and translated according to the orientation information to register with the high-density sub-objects in the scanned object. An optimization process with iterations described above is used here to minimize the registration error. Once the shape images are registered with the high-density sub-objects in the scanned object, high density sub-objects can be segmented from the reconstructed images by the shape images multiplying the reconstructed images. The segmented high density sub-objects are then forward-projected onto the detector to obtain the projections containing high density sub-objects only at each angular location. Once the projections during the entire scan are acquired, their second and third order projections are calculated and weighted by the corresponding polynomial parameters, which were obtained previously under the same x-ray spectrum. The weighted high order projections are then added to the original projections of the scanned object to get corrected projections. Finally, the corrected projections are reconstructed to achieve artifacts-reduced images of the object, as illustrated in FIG. 5C-D.

Figure 6:
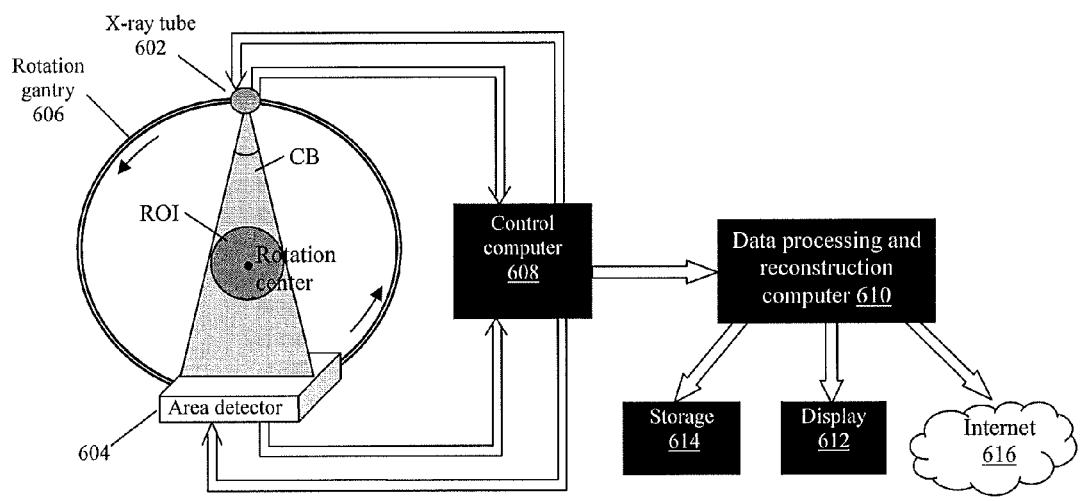
FIG. 6 shows a block diagram of a system on which the preferred embodiment can be implemented.

FIG. 6 shows a block diagram of a system on which the preferred embodiment or other embodiments can be implemented. In the system 600, an x-ray source 602 and a two-dimensional area or flat-panel detector 604 are mounted on a circular rotation gantry 606. The x-ray source 602 emits a cone beam CB that passes through a region of interest ROI and is incident on the detector 604. The source 602 and detector 604 are both in communication with a control computer 608, which performs the operations described above and obtains projections. Once the projections are acquired they are transferred from the control computer 608 to a data processing and reconstruction computer 610 for image reconstruction. The resulting images can be displayed on a display 612, stored in storage 614, or transmitted over the Internet or another communication medium 616 to a remote user. The storage 614 can also be used to store the libraries mentioned above, which can be prepared in advance or on the fly.

While a preferred embodiment of the invention has been set forth in detail with reference to the drawings, those skilled in the art who have reviewed the present disclosure will readily appreciate that other embodiments can be realized within the scope of the invention. For example, numerical values are illustrative rather than limiting, as are disclosures of specific imaging technologies. For example, any 3D imaging technique, such as fan-beam computed tomography, can be used. Also, as noted above, the invention is not limited to the imaging of titanium objects or of bone grafts. Moreover, there is no reason why the image data have to be taken and processed at the same time or in the same place; instead, they could be transmitted off-site over the Internet or another suitable communication medium for processing or stored for later processing. Therefore, the present invention should be construed as limited only by the appended claims.

We claim:

1. A method for producing an image of a region of interest while correcting artifacts caused by sub-objects within the region of interest, the method comprising:
   (a) receiving three-dimensional image data of the region of interest;
   (b) receiving a library of shape information and imaging characteristics of the sub-objects;
   (c) using the three-dimensional image data and the library to produce images of the sub-objects in the region of interest;
   (d) using an optimization process to produce segmented images of the sub-objects in the region of interest;
   (e) using the segmented images to produce error projections; and
   (f) using the error projections to produce the projection images of the region of interest such that the artifacts are corrected in the image;
   (g) performing a tomographically reconstructed image of the region of interest from the corrected projection images.

2. The method of claim 1, wherein the three-dimensional image data comprise computed tomography image data.

3. The method of claim 2, wherein the computed tomography image data are cone-beam or fan-beam computed tomography image data.

4. The method of claim 1, wherein step (a) comprises taking the three-dimensional image data.

5. The method of claim 1, wherein step (a) comprises receiving the three-dimensional image data previously formed on a storage medium or over a communication medium.

6. The method of claim 1, wherein step (b) comprises receiving the library previously formed on a storage medium.

7. The method of claim 1, wherein step (b) comprises forming the library through scanning, reconstruction and information extraction performed on the sub-objects.

8. The method of claim 1, wherein step (e) comprises determining an amount of beam hardening caused by the sub-objects.

9. The method of claim 8, wherein step (e) further comprises calculating a polynomial function of a line integral of the beam hardening.

10. The method of claim 1, wherein the sub-objects comprise metal objects causing metal artifacts in the images.

11. The method of claim 1, wherein the optimization process is iterative.

12. A system for producing an image of a region of interest while correcting artifacts caused by sub-objects within the region of interest, the system comprising:
- a device for receiving three-dimensional image data of the region of interest;
- a device for receiving a library of shape information and imaging characteristics of the sub-objects;
- a processor, having access to the three-dimensional image data and the library, the processor being configured for:
  - (i) using the three-dimensional image data and the library to produce images of the sub-objects in the region of interest;
  - (ii) performing an optimization process to produce segmented images of the sub-objects in the region of interest;
  - (iii) using the segmented images to produce error projections; and
  - (iv) using the error projections to produce the projection images of the region of interest such that the artifacts are corrected in the projection images; and
  - (v) obtaining tomographically-reconstructed image of the region of interest from the corrected projection images an output for outputting the reconstructed image of the region of interest.

13. The system of claim 12, wherein the processor is configured such that the three-dimensional image data comprise computed tomography image data.

14. The system of claim 13, wherein the processor is configured such that the computed tomography image data are cone-beam or fan-beam computed tomography image data.

15. The system of claim 12, wherein the device for receiving the three-dimensional image data comprises a device for taking the three-dimensional image data.

16. The system of claim 12, wherein the device for receiving the three-dimensional image data comprises a device for receiving the three-dimensional image data previously formed on a storage medium or over a communication medium.

17. The system of claim 12, wherein the device for receiving the library comprises a device for receiving the library previously formed and provided on a storage medium.

18. The system of claim 14, wherein the processor is configured to determine an amount of beam hardening caused by the sub-objects.

19. The system of claim 18, wherein the processor is further configured to calculate a polynomial function of a line integral of the beam hardening.

\* \* \* \* \*